United States Patent [19]
Chau

[11] Patent Number: 5,371,586
[45] Date of Patent: Dec. 6, 1994

[54] LOW ABERRATION DIFFRACTION GRATING SYSTEM

[75] Inventor: Chiu Chau, Woodbridge, N.J.
[73] Assignee: Instruments SA, Inc., Edison, N.J.
[21] Appl. No.: 960,091
[22] Filed: Oct. 9, 1992
[51] Int. Cl.[5] .................. G01N 21/64; G01N 21/65
[52] U.S. Cl. ........................... 356/301; 356/318; 356/328; 356/334; 250/458.1
[58] Field of Search .......... 356/300, 301, 318, 326, 356/328, 331, 332, 334; 250/458.1, 459.1, 461.1, 461.2

[56] References Cited

U.S. PATENT DOCUMENTS

| | | | |
|---|---|---|---|
| Re. 32,735 | 8/1988 | Clay et al. | 250/566 |
| 4,351,611 | 9/1982 | Leif | 356/328 |
| 5,048,960 | 9/1991 | Hayashi et al. | 356/319 |

FOREIGN PATENT DOCUMENTS

55822 5/1981 Japan ................... 356/334

*Primary Examiner*—F. L. Evans
*Attorney, Agent, or Firm*—Handal & Morofsky

[57] ABSTRACT

A light analysis system is disclosed and comprises a source of substantially collimated light to be analyzed. The source comprises a sample excited by a collimated laser light source, and further comprises a holographic notch filter having the characteristic of reflecting light at the excitation wavelenghth at which the source is excited. An aberration corrected concave focusing diffraction grating receives the collimated light and focuses it at a point corresponding to its wavelength. A detector detects light at a desired wavelength focused by the diffraction grating. The holographic notch filter is positioned to filter the source of substantially collimated light to be filtered and the holographic notch filter is oriented substantially at an angle with respect to the collimated laser light source to result in a path length for the collimated laser light source which constrains a path length through the notch filter which causes the collimated laser light to be reflected by the filter away from the grating. The grating is an aberration corrected concave focusing diffraction grating. The collimated light is in the form of a bundle having a width on the order of ten millimeters.

11 Claims, 4 Drawing Sheets

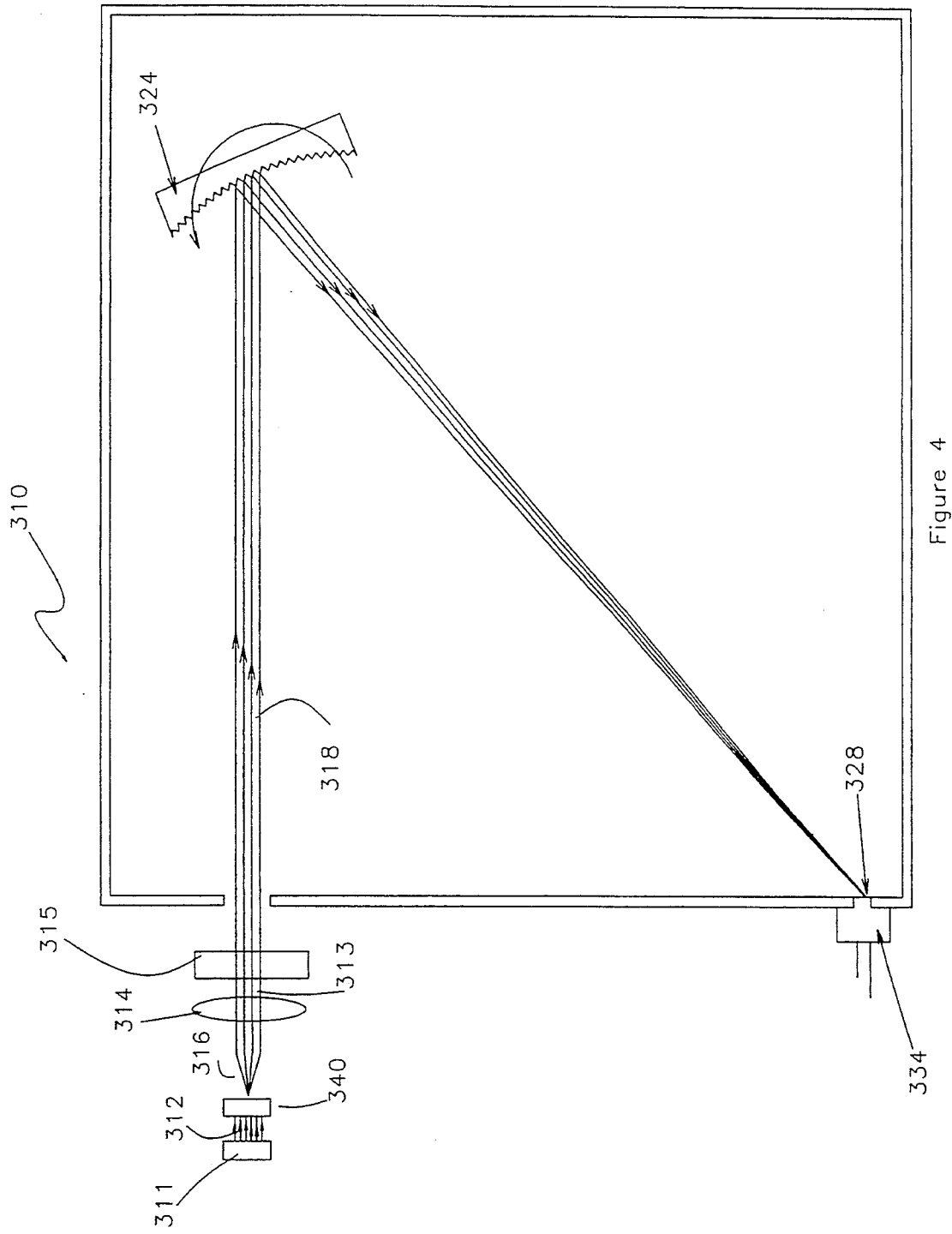

LOW ABERRATION DIFFRACTION GRATING SYSTEM

TECHNICAL FIELD

The present invention relates to monochromators and spectrometers and, in particular, such devices of this type which incorporate filters in the input light path.

BACKGROUND

The technology of using gratings to analyze the wavelength content of incident light dates back to about 1786, when the American astronomer David Rittenhouse made a grating by arranging fifty or sixty hairs in the threads of a pair of miniscule brass screws at a pitch of 106 to the inch. Rittenhouse noted his surprise that red ray paths were bent more than blue ray paths and that a single slit source generated three parallel lines of light.

About a century later, Lord Rayleigh recorded the first holographic diffraction grating and noted its properties. However, classical ruled gratings remained the standard until the 1960's when Flamand applied a heuristic approach to solve the problem of the aberrations in reflective diffraction gratings. This made possible the now extensive use of aberration corrected holographic gratings that we have today.

More recently, the availability of computers of previously almost unimaginable power, has resulted in the development of numerous low aberration grating designs. These are made by using the computer to simulate the recording of the grating at various recording points. By trial and error, exploring variations of recording parameters about known or intuitively favorable starting points, one simulates the manufacture and evaluation of extremely large numbers of gratings. This information determines a high quality design for a particular purpose.

As noted above, the concave holographic aberration corrected grating is extensively used today. Its advantages lie in the simplicity of the mounting system and the relatively low cost of the commonly used grating replicas, which are formed by a molding process from a photographically recorded grating original. Considering the mounting, there have been numerous mountings proposed over the years, each of which has its particular advantages and weak points.

Perhaps the oldest mounting for a concave grating is the so-called Rowland circle configuration. Here, the surface of the grating and an input slit for providing incident light to the grating are positioned on the circle defined by the concave surface of the so-called Rowland grating. With this type of grating, a spectrum is formed on a focal surface which also lies on this circle, known as the Rowland circle. In this manner, a detector or array may be placed at the focal surface to detect, for example, a number of discrete wavelengths. Alternatively, if desired, the configuration may be modified to act as a monochromator, by putting a second output slit at that point on the focal surface on the Rowland circle where light of a desired wavelength is focused.

Another popular mount is the so-called Seya-Namioka configuration where an inlet slit provides light to a focusing aberration corrected grating, with a desired wavelength being detected at an output point typically comprising an outlet slit and photodetector. Wavelength selection is achieved by rotation of the grating about its axis.

Still yet another configuration for using a concave grating is the Wadsworth mounting, in which the grating is illuminated by collimated light. In the Wadsworth mounting, light from an inlet slit is collimated by a large concave mirror and caused to fail upon the grating. The grating then creates a spectrum which is positioned on a focal surface at a distance of approximately half the radius of curvature of the grating.

As can be seen from the above, various spectrographic systems typically operate with an inlet slit and various types of output configurations such as slits, array detectors, or the like. Naturally, merely analyzing light, divorced from a particular physical system, is of limited interest. Rather, the applications of spectrographic analysis are of primary importance. Such applications include passing light through a sample of material and noting the emission spectra in the form of Raman, fluorescence or similar effects. In addition, a sample may be excited by energy other than light, such as electrical energy.

In any case, present industrial practice generally involves the excitation of a sample and the focusing of the emitted light onto the inlet slit of a monochromator or spectrometer. The sample can be a blood sample, a tissue sample, an oil sample or any of these materials in a desired emulsion or solution, or other sample prepared in accordance with techniques known in the art.

In a typical Raman application, light from a solid state laser diode having a bundle diameter on the order of one or two millimeters is used. This "pencil" of light may be used directly or expanded using appropriate optics to a wider collimated pencil of light. This pencil of light is caused to fall upon a sample causing emission of scattered light which is collimated by a concave lens into a relatively wide bundle, typically having a dimension on the order of ten millimeters in diameter. This bundle is sometimes caused to pass through a holographic notch filter where the wavelength of the excitation light is removed. After this the light is focused by a convex lens onto the inlet slit of a monochromator which takes any one of the numerous popular monochromator configurations.

The use of the above filter for filtering out the excitation wavelength, while a common practice today, introduces numerous distortions into the system because of the need for double optics for collimating the scattered light and refocusing it after collimation. However, such collimation is required on account of the fact that the holographic notch filter, in order to operate properly, must receive collimated light. More particularly, such holographic notch filters comprise a volume phase hologram inside a thin holographic film. Volume phase holograms operate on an interference principle in which numerous internal planes with known separations therebetween operate to create destructive interference of light at precise wavelengths. For example, the result of such interference may be substantially 100% reflection for a filter designed to operate at 536 nanometers, within a narrow bandwidth of only two nanometers.

However, in accordance with Bragg's law, interference is a function of the distance encountered by light passing through one plane onto another. The encountered distance varies depending upon the angle of incidence to the filter surface. Thus, there will be a wavelength shift proportional to the angle of incidence to the hologram. Thus, if one wishes to remove a particular wavelength, the relationship of angles between the incident light which one wishes to pass and the incident light which one wishes to reject are ideally the same and the distance between the planes in the volume phase hologram which comprises the notch filter is selected for substantially complete reflection. This is particularly important in view of the fact that the amplitude of light at the source may be on the order of a million times the magnitude of the emitted signal. Some idea of the difficulty of the problem involved in this design may be seen when one considers that oftentimes a sample is illuminated with light at, for example, 536 nanometers and one desires to measures light emitted at a wavelength of 540 nanometers.

SUMMARY OF THE INVENTION

The invention, as claimed, is intended to provide a remedy to the problem of selectively removing the excitation wavelength without the need for input collimating optics. The same is achieved through the provision of a system in which collimated light is caused to fall on a grating after filtering with or without the customary monochromator or spectrometer inlet slit. More particularly, in accordance with the inventive system, a wide pencil of collimated light, typically on the order of ten millimeters in width is passed through a cell containing a sample of material and then passed through a holographic notch filter positioned at an angle with respect to the collimated light which results in rejection by complete reflection of light at the excitation wavelength. The light then falls on a concave holographic grating which is designed to have the characteristic of focusing light of a particular wavelength at an outlet slit. In accordance with the preferred embodiment, the outlet slit and an input port having a diameter of about ten millimeters are both defined in a housing containing the diffraction grating.

BRIEF DESCRIPTION OF THE DRAWINGS

One way of carrying out the invention is described in detail below with reference to drawings which illustrate only one specific embodiment of the invention and in which:

FIG. 4 is still another alternative embodiment of the invention in which a sample is excited by a laser like source and in which the grating may be optionally rotated in order to selectively measure light at different wavelengths.

BEST MODE FOR CARRYING OUT THE INVENTION

Figure 1:
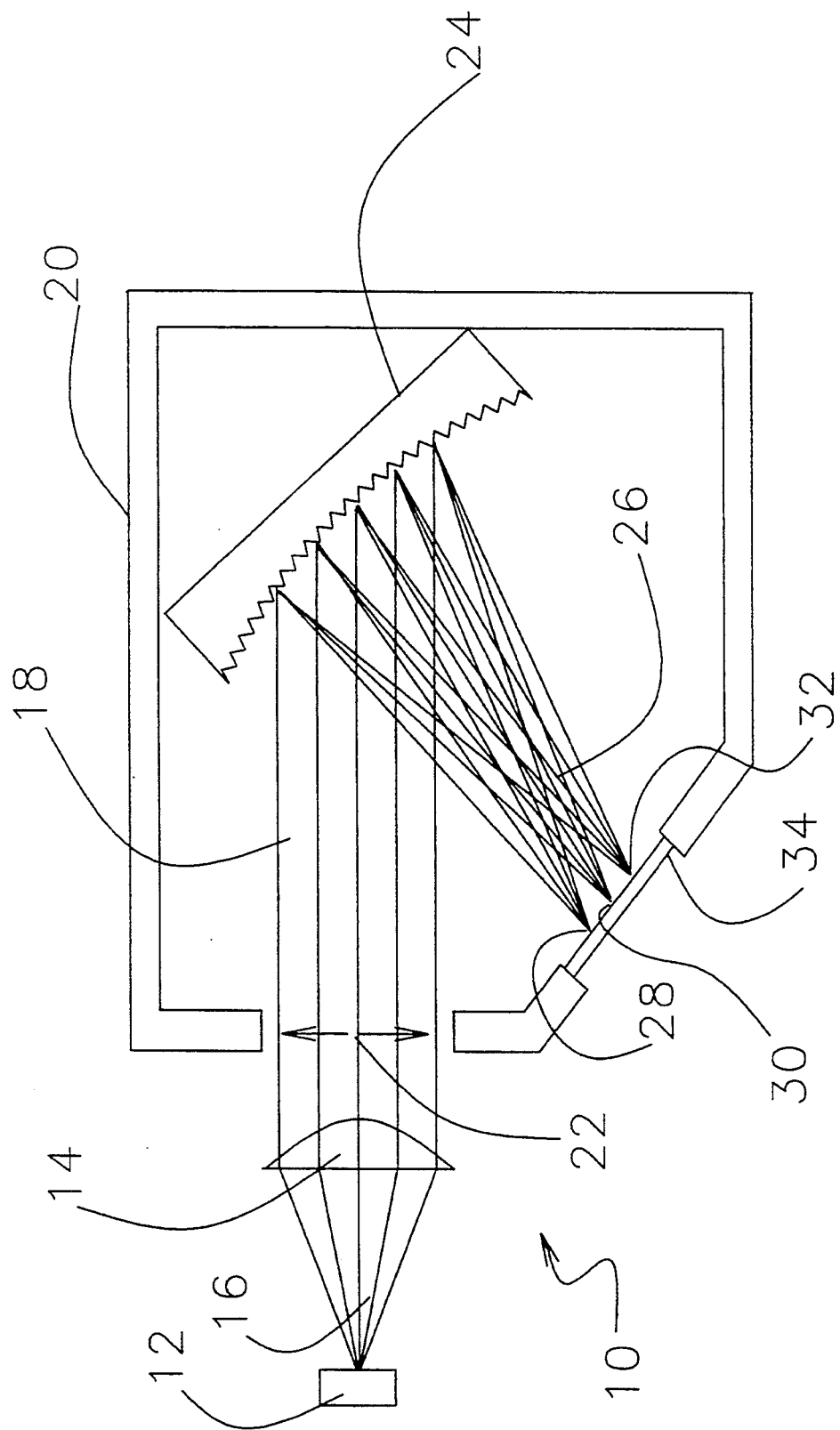
FIG. 1 is a diagram of a spectrometer constructed in accordance with the present invention.

Referring to FIG. 1, a system incorporating a spectrometer constructed in accordance with the present invention is illustrated. System 10 generally comprises a source 12 of radiation to be analyzed. Such source may be in the ultraviolet, infrared or visible portion of the electro magnetic spectrum in a typical case. Source 12 is generally a source which emits light within a single plane, which corresponds with the focal plane of collimating lens 14. Thus, light 16 emitted from source 12 is collimated into a parallel bundle 18 by collimating lens 14.

After being collimated, the light forming collimated bundle 18 passes into the housing 20 through an inlet port 22. Inlet port 22 is of relatively large dimension compared to a typical input slit on a monochrometer or spectrometer subassembly housing. In particular, input port 22 would typically be of circular shape and have a diameter on the order of about 10 millimeters. After passing into housing 20, collimated bundle 18 is caused to fall on a diffraction grating 24. After striking diffraction grating 24, collimated light bundle 18 is reflected and focused as a reflected bundle 26.

More particularly, the collimated light is broken up into its constituent wavelength components and focused at positions which are a function of the particular wavelengths involved the illustrated example, if we consider bundle 18 to comprise light of three wavelengths, each of these wavelengths is separated and focused at a discrete point corresponding to points 28, 30 and 32. Thus, with the provision of an array or area detector 34, light of each wavelength is detected by a separate detecting element in the detector, with the identity of the particular detector being excited by the reflected light bundle 26 indicating the existence of light at its corresponding associated wavelength. In particular, it is noted that the system employs an array detector which has a plurality of detector points at a plurality of positions corresponding to the positions associated with particular wavelengths for grating 24. Thus, the amplitude and existence of various wavelengths may be detected using detector 34.

Figure 2:
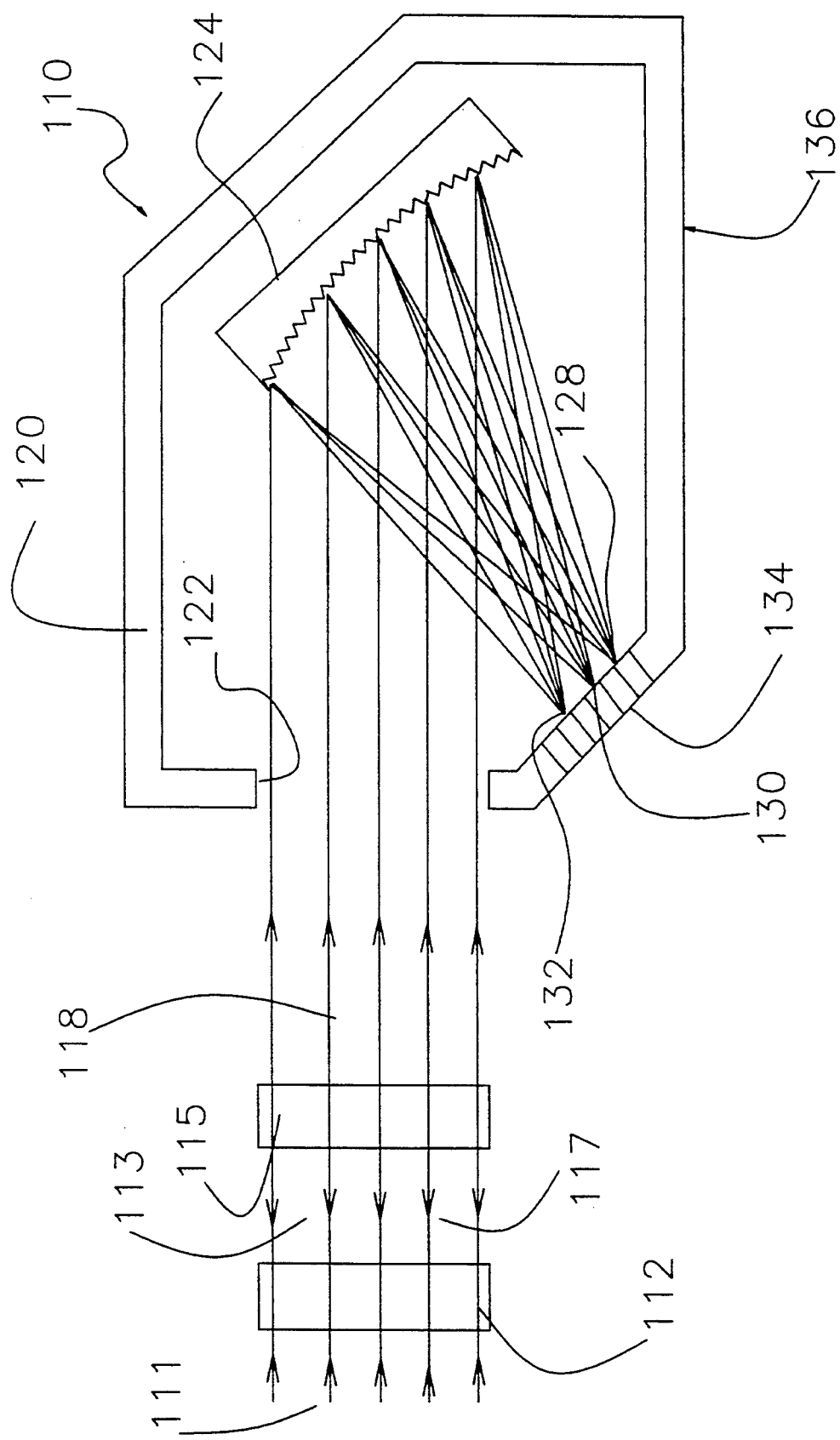
FIG. 2 is a diagram of a spectrometer constructed in accordance with the present invention and using a holographic notch filter.

In FIG. 2, the system 110 is driven by a collimated input light bundle 111 and passes through a sample 112 causing the emission of light at a wavelength different from the excitation wavelength of bundle 111. In a typical application, bundle 111 is a collimated light bundle produced by a laser and having a single wavelength. Bundle 111 falls on sample 112 causing sample 112 to emit fluorescent or Raman emissions which have a wavelength different from that of bundle 111. However, in many applications, the wavelength of the light 113 emitted by sample 112 when it is excited by light at the wavelength of bundle 111 may be very close to the wavelength of light in bundle 111. It thus becomes necessary to remove light having the wavelength of bundle 111 which has passed through sample 112. Accordingly, a filter 115 is used to reflect light that portion of incident light 117 which has the same wavelength as bundle 111. In accordance with the preferred embodiment, filter 115 is a so-called holograhic-notch filter of the type using a volume-phase hologram recorded in a polymeric holographic material, such as dichromate of gelatin or other material suitable for recording a volume-phase hologram. Filter 115 may be a Raman hololgraphic edge filter of the type manufactured by Physical Optics Corporation of Torrance, Cal. Accordingly, the light 118 which is passed by holographic notch filter 115 is passed through an inlet port 122 in housing 120, where it falls upon a diffraction grating 124. In many circumstances, the emitted light 118 falling on the grating and input into the spectrometer module 136 has a number of emitted wavelengths and each of these wavelengths is focused at different points, illustrated as points 128, 130 and 132 in FIG. 2. This, in a matter similar to that of the system of FIG. 1, results in excitation of an array or area detector 134 and the detection of the wavelength content and relative intensity across the emitted spectrum.

The embodiment illustrated in FIG. 2 is particularly advantageous insofar as the system provides for a collimated bundle for rejection of the excitation wavelength within a very narrow range and thus even the rejection of the excitation wavelength when it is very close to the emitted wavelength. This results in extremely high signal-to-noise ratios, even where the excitation wavelength is a few nanometers displaced from the emitted wavelength and has an amplitude of hundreds of thousands of times the amplitude of the signal.

In accordance with the preferred embodiment, it is believed that the signal-to-noise ratio achievable with the system of FIG. 2 high enough to make practical the use of such systems conjunction with refrigerated detector systems and relatively long exposure periods.

In addition, the system of the present invention results in not only extremely high signal-to-noise ratio, but also extremely high resolution between adjacent emission wavelengths. In particular, because of the fact that the system eliminates the additional convex lens or other focusing optic necessary to bring the collimated bundle into an inlet slit, the number of distortions introduced into the system is reduced by the reduction of the number of elements.

In addition, there is a somewhat more subtle effect in-so-far as the grating as being excited with a collimated bundle. This provides an additional reduction in distortion of the system and an improvement in resolution. More particularly, this effect may be understood by considering the equation describing the operation of an aberration corrected grating:

$$\Delta = -Y\left[\operatorname{SIN}\alpha + \operatorname{SIN}\beta - k\frac{\lambda}{\lambda_o}(\operatorname{SIN}\gamma - \operatorname{SIN}\delta)\right] +$$

$$\frac{Y^2}{2}\left[\frac{\cos^2\alpha}{l_A} - \frac{\cos\alpha}{R} + \frac{\cos^2\beta}{l_B} - \frac{\cos\beta}{R} - \right.$$

$$k\frac{\lambda}{\lambda_o}\left(\frac{\cos^2\gamma}{l_C} - \frac{\cos\gamma}{R}\right) +$$

$$\left. k\frac{\lambda}{\lambda_o}\left(\frac{\cos^2\delta}{l_D} - \frac{\cos\delta}{R}\right)\right] +$$

$$\frac{Z^2}{2}\left[\frac{1}{l_A} - \frac{\cos\alpha}{R} + \frac{1}{l_B} - \frac{\cos\beta}{R} - \right.$$

$$\left. k\frac{\lambda}{\lambda_o}\left(\frac{1}{l_C} - \frac{\cos\gamma}{R}\right) + k\frac{\lambda}{\lambda_o}\left(\frac{1}{l_D} - \frac{\cos\delta}{R}\right)\right] +$$

$$\frac{Y^3}{2}\left[\frac{\operatorname{SIN}\alpha}{l_A}\left(\frac{\cos^2\alpha}{l_A} - \frac{\cos\alpha}{R}\right) + \right.$$

$$\frac{\operatorname{SIN}\beta}{l_B}\left(\frac{\cos^2\beta}{l_B} - \frac{\cos\beta}{R}\right) -$$

$$k\frac{\lambda}{\lambda_o}\frac{\operatorname{SIN}\gamma}{l_C}\left(\frac{\cos^2\gamma}{l_C} - \frac{\cos\gamma}{R}\right) +$$

-continued $$\left. k\frac{\lambda}{\lambda_o}\frac{\operatorname{SIN}\delta}{l_D}\left(\frac{\cos^2\delta}{l_D} - \frac{\cos\delta}{R}\right)\right]$$

Where $\Delta$ = Aberrated optical path (a measure of aberration)
Y = Coordinates on axis from an origin at the center of the grating surface and extending perpendicular to the grating surface.
Z = Coordinates on axis from an origin at the center of the grating surface and extending parallel to the grooves of the grating surface.
$\alpha$ = Incident light angle
$\beta$ = Deflected angle
K = Order of diffraction
$\lambda$ = Output wavelength, user wavelength
$\lambda_0$ = Recording wavelength for hologram grating
$l_A$, $\alpha_32$ Polar coordinates of entrance point
$l_B$, $\beta$ = Polar coordinates of exit point
$l_C$, $\delta$ = Polar coordinates of first recording point of holographic grating
$l_D$, $\delta$ = Polar coordinates of second recording point of holographic grating
R = Radius of the spherical blank (curvature of grating).

As can be seen from analysis of the above equation, the use of collimated light results in $l_A$ being equal to infinity, thus reducing the distortions and the aberration in the system.

Figure 3:
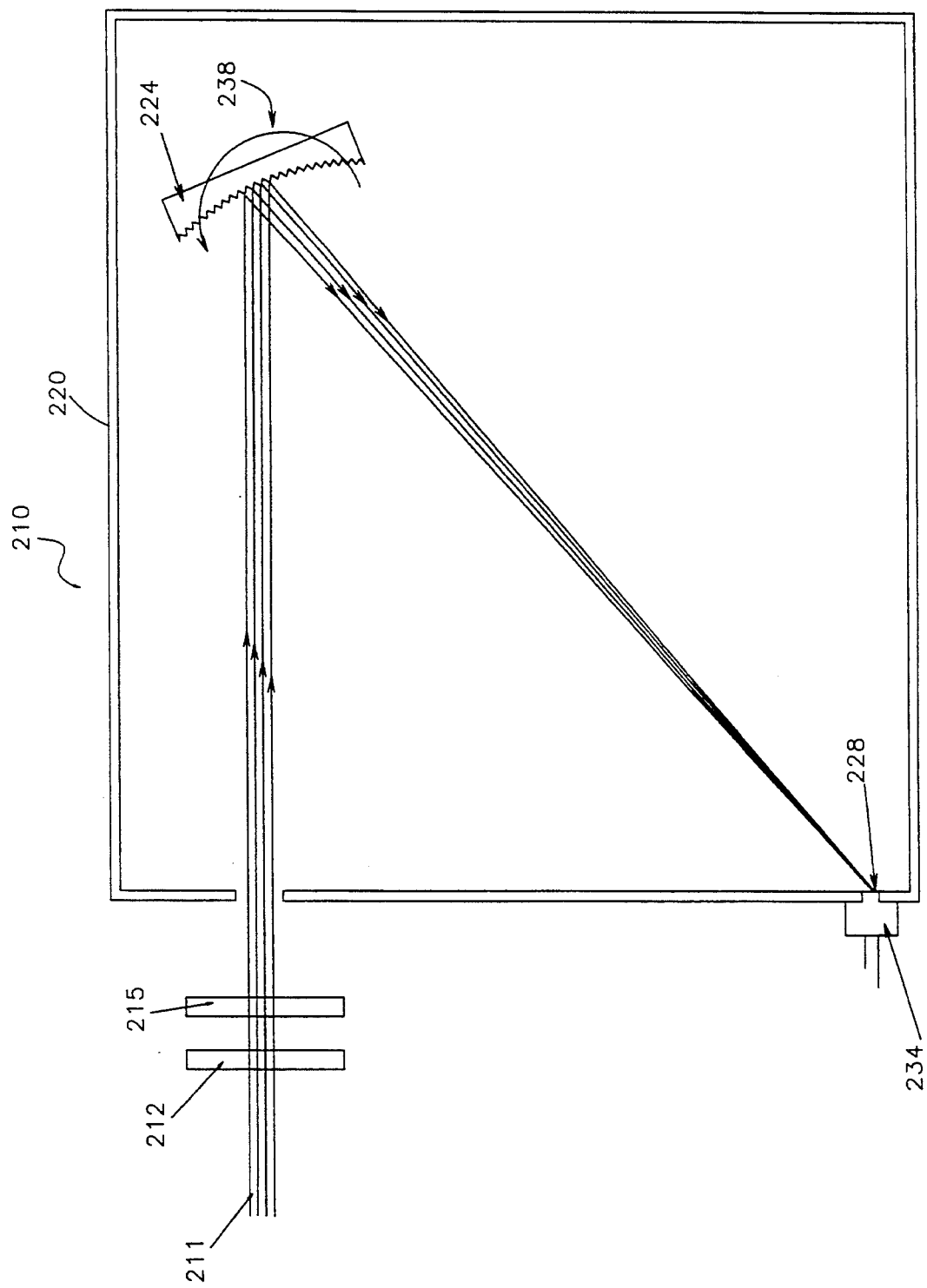
FIG. 3 is a diagram of a monochromater incorporating a mounting arrangement constructed in accordance with the present invention and using a photomultiplier tube.

Referring to FIG. 3, a system similar to that illustrated in FIG. 2 is illustrated. In particular, system 210 includes a sample 212 which is excited by incident radiation 211 from a laser or other suitable source and is filtered by holographic notch filter 215. Here again, a housing 220 contains a grating 224 which focuses light at an output point 228 where it is detected by a suitable detector such as a photomultiplier tube 234. In accordance with the preferred embodiment, grating 224 may be mounted in a fixed position or the grating may be used to selectively determine the existence of radiation at various wavelengths by being mounted on a mounting which permits rotation as indicated by arrow 238.

Referring to FIG. 4, a system similar to that illustrated in FIG. 3 is shown. Here, system 310 is provided with input energy from a laser 311. Laser 311 produces light 312 which is caused to fall on a sample 340 which emits light 316. Light 316 passes through lens 314 which collimates the light into a bundle 313. Bundle 313 passes through a holographic notch filter 315 which reflects light at the excitation wavelength. Filtered light 318 is then caused to fall upon a diffraction grating 324, which may be mounted in a fixed position or rotated to selectively image light at a wavelength to be detected at a point 328 for detection by a photomultiplier 334 or other suitable detector.

While an illustrative embodiment of the invention has been described above, it is, of course, understood that various modifications will be apparent to those of ordinary skill in the art. Such modifications are within the spirit and scope of the invention, which is limited and defined only by the appended claims.

I claim:

1. A light analysis system, comprising:
   (a) a source of substantially collimated light to be analyzed, said collimated light being in the form of a bundle having a width with a magnitude on the order of ten millimeters;

(b) an aberration corrected concave focusing diffraction grating for receiving said collimated light and focusing it at a point corresponding to its wavelength; and (c) a detector for detecting light at a desired wavelength focused by said diffraction grating.

2. A system as in claim 1, wherein said collimated light is filtered by a holographic notch filter.

3. A system as in claim 1, wherein said detector is a photomultiplier tube.

4. A system as in claim 1, wherein said detector is an array detector.

5. A system as in claim 1, wherein said detector is an area detector.

6. A system as in claim 1, wherein said grating is rotated to select a desired wavelength.

7. A system as in claim 1, wherein said source comprises a collimated laser light source generating collimated laser light and a sample excited by said collimated laser light source to generate said light to be analyzed, and said system further comprising a holographic notch filter receiving said light to be analyzed and having the characteristic of reflecting light at the excitation wavelength at which said sample is excited, said holographic notch filter being positioned to filter said source of substantially collimated light to be analyzed and said holographic notch filter being oriented substantially at an angle with respect to said collimated laser light source which results in a path for said collimated laser light source which constrains a path length through said notch filter which causes that portion of said collimated laser light which passes through said sample to be reflected by said filter away from said grating.

8. A system as in claim 1, wherein said source comprises a light source positioned to excite a sample to emit emitted light and collimating optics to collimate said emitted light.

9. A light analysis system, comprising:
(a) a source of substantially collimated light to be analyzed, said source comprising a collimated laser light source generating collimated laser light and a sample excited by said collimated laser light source to emit said light to be analyzed;
(b) a holographic notch filter positioned with respect to said sample to filter light emitted by said sample and to have the characteristic of reflecting light at the excitation wavelength at which said sample is excited;
(c) an aberration corrected concave focusing diffraction grating for receiving said filtered collimated light and focusing it at a point corresponding to its wavelength; and
(d) a detector positioned at said point for detecting light at a desired wavelength focused by said diffraction grating.

10. A system as in claim 9, wherein said holographic notch filter is positioned to filter said source of substantially collimated light to be analyzed and said holographic notch filter is oriented substantially at an angle with respect to said collimated laser light source which results in a path for said collimated laser light source which constrains a path length through said notch filter which causes that portion of said collimated laser light which passes through said sample to be reflected by said filter away from said grating.

11. A light analysis system, comprising:
(a) a source of substantially collimated light to be analyzed, said source comprising a laser light source generating laser light and a sample excited by said laser light source to emit said light to be analyzed;
(b) an optical element for collimating said light to be analyzed;
(c) a holographic notch filter receiving said light to be analyzed and having the characteristic of reflecting light at the excitation wavelength at which said sample is excited;
(d) an aberration corrected concave focusing diffraction grating for receiving said collimated light and focusing it at a point corresponding to its wavelength, said grating being mounted for rotation to select the focussing of a desired wavelength at said point; and
(e) a detector for detecting light at a desired wavelength focused by said diffraction grating, wherein said holographic notch filter is positioned to filter said source of substantially collimated light to be analyzed and said holographic notch filter is oriented substantially at an angle with respect to said collimated laser light source which results in a path for said collimated laser light source which constrains a path length through said notch filter which causes that portion of said collimated laser light which passes through said sample to be reflected by said filter away from said grating, and said collimated light is in the form of a bundle having a width with a magnitude on the order ten millimeters.

* * * * *